United States Patent [19]
Ahmad et al.

[11] Patent Number: 5,588,959
[45] Date of Patent: Dec. 31, 1996

[54] HEMODIALYSIS RECIRCULATION MEASURING METHOD

[75] Inventors: Suhail Ahmad, Seattle; James J. Cole, Arlington; Mahboob Ahmed, Bothell, all of Wash.

[73] Assignee: University of Washington, Seattle, Wash.

[21] Appl. No.: 288,678

[22] Filed: Aug. 9, 1994

[51] Int. Cl.$^6$ .......................... A61M 37/00; A61M 1/00
[52] U.S. Cl. ..................................... 604/6; 604/28; 604/4
[58] Field of Search ............................................. 604/4, 28

[56] References Cited

U.S. PATENT DOCUMENTS 4,808,159  2/1989  Wilson ......................................... 604/4

FOREIGN PATENT DOCUMENTS 3817603  11/1989  Germany ..................................... 604/4

OTHER PUBLICATIONS

Greenwood et al., "Assessment of arteriovenous fistulae from pressure and thermal dilution studies: Clinical experience in forearm fistulae", Clinical Nephrology 23:189, 1985.

Tattersall et al., Nephrol. Dial. Transplant 8:60, 1993.

*Primary Examiner*—David H. Willse
*Assistant Examiner*—Mark O. Polutta
*Attorney, Agent, or Firm*—Jeffrey B. Oster

[57] ABSTRACT

There is disclosed a method for rapidly and inexpensively determining the amount of recirculation in a patient undergoing a dialysis treatment comprising measuring temperature of an arterial limb and a venous limb of a dialysis access, decreasing temperature of blood being returned to the patient from about 0.5° C. to about 30° C. without adding volume, and measuring temperature of the arterial limb and the venous limb of the dialysis access to determine if there is a temperature drop in the arterial limb as evidence of recirculation. There is further disclosed an improved blood tubing set for use in dialysis and for simultaneously determining recirculation according to the inventive method herein, comprising a blood tubing set having an arterial limb comprising an arterial access device and an arterial tube and having a venous limb comprising a venous access device and a venous tube, wherein an access device comprises a means for obtaining or returning blood from or to an individual, wherein the improvement comprises a means for measuring temperature in the arterial limb and a means for measuring temperature in the venous limb.

5 Claims, 5 Drawing Sheets

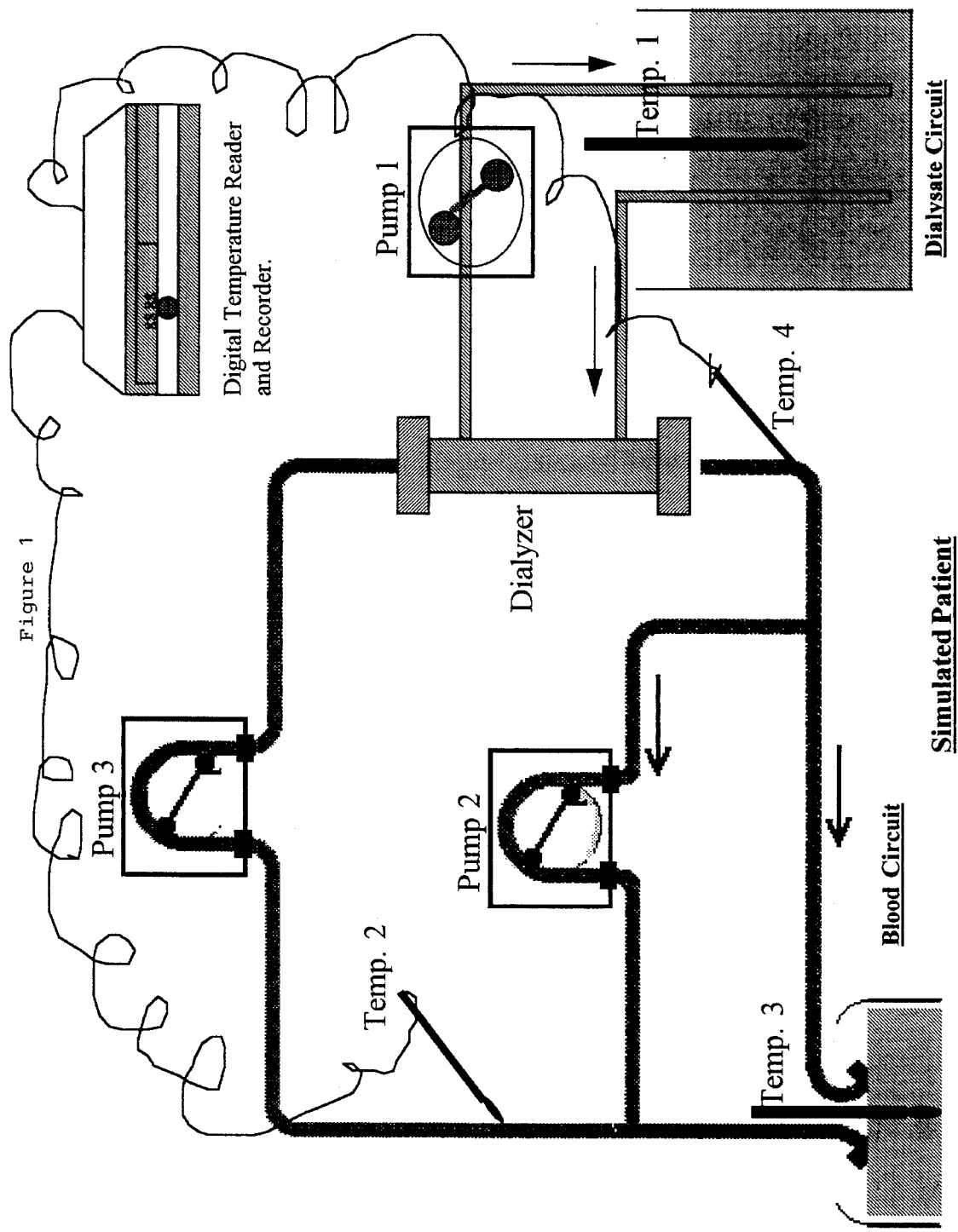

Figure 4
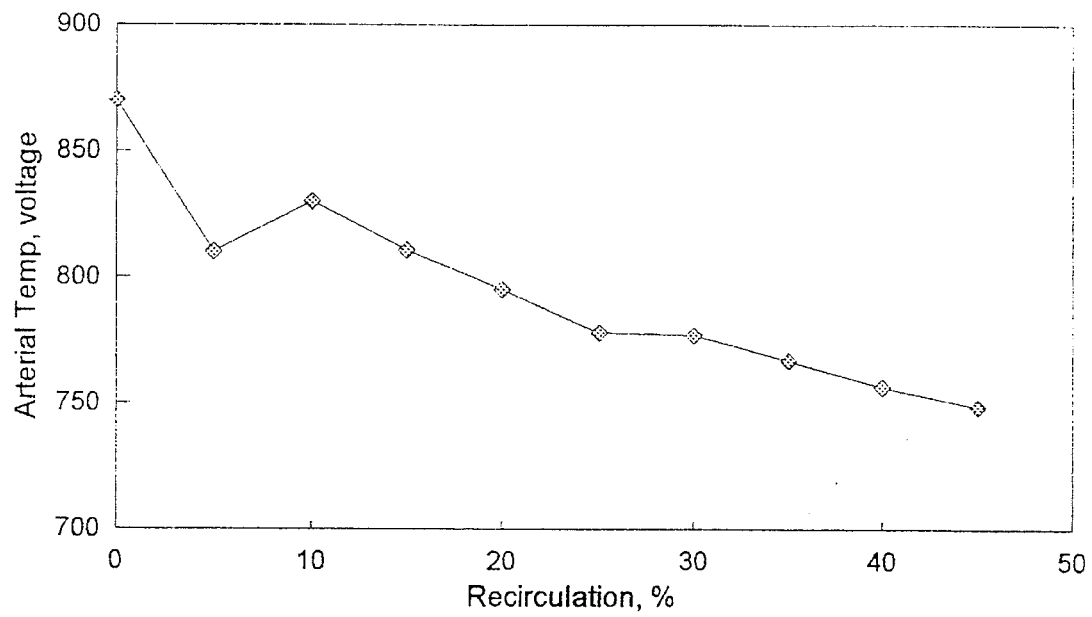
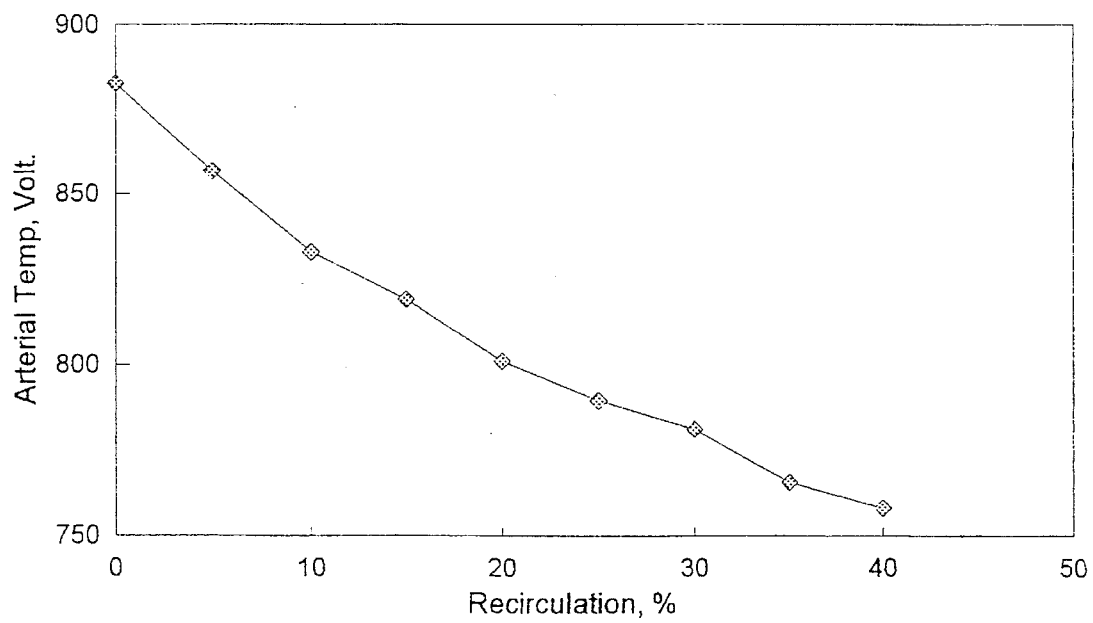

HEMODIALYSIS RECIRCULATION MEASURING METHOD

TECHNICAL FIELD OF THE INVENTION

The present invention provides a hemodialysis recirculation measuring system that can instantly determine the amount of "recirculation" present, if any, when blood is accessed for extracorporeal treatment. Specifically, the present invention provides a means for measuring the temperature of the "arterial" and "venous" limbs of blood access and changing the temperature of blood being returned to the patient via the venous limb to measure the amount of recirculation as determined by a change in the temperature of blood in the arterial limb.

BACKGROUND OF THE INVENTION

Successful hemodialysis and hemofiltration require access to the circulatory system, often by means of an arteriovenous fistula or graft. Extracorporeal blood flow rates above 200 ml/min are essential for efficient hemodialysis and hemofiltration. Many patients experience dialysis vascular access (e.g., fistula) problems which produce extracorporeal blood flow rates that are suboptimal. If vascular access cannot supply fresh blood at a rate demanded by the dialysis blood pump, a portion of blood returning from the dialysis machine, via a venous line, recirculates back to the machine via the arterial line, instead of returning to the patient. The quantity of this recirculation will directly influence the efficiency of the dialysis process. Ideally, zero recirculation is desired and when this recirculation is in excess of 10% of returning blood, the efficiency of dialysis is adversely affected.

One essential element for improving dialysis patient care is the effective and speedy detection and measurement of recirculation. Recirculation during dialysis can be caused by a variety of factors, such as: (1) improper placement of needles in the vascular access, (2) narrowing (stenosis) of fistulae or graft structure, (3) improper position of catheter ends, or (4) mechanical obstruction of venous line or venous limbs of the vascular access. Despite this common problem, there has been no satisfactory, inexpensive, simple and objective method of assessing recirculation.

Over the past decade, there has been a deliberate attempt to increase the efficiency of dialysis by increasing blood flow rates in order to reduce dialysis treatment times. For such modes of high efficiency dialysis, a blood flow rate in excess of 300 ml/min is required. However, this high blood flow rate may increase the amount of recirculation, directly impacting the efficiency of dialysis.

One method for detecting recirculation is the saline bolus injection method described by Greenwood et al., *Clinical Nephrology* 23:189, 1985. This method involves a chilled saline bolus injected into the venous blood line that can be detected by a drop in temperature in the arterial line in the presence of recirculation. According to a later article by the same group of authors (Tattersall et al., *Nephrol. Dial. Transplant.* 8:60, 1993), the method "requires special equipment such as the fistula assessment monitor (FAM, Gambro)." This method requires that the pumps be adjusted downward, initially to about 100 ml/min, in order to make the recirculation measurement determination. This procedure, in itself, is time consuming and greatly increases dialysis time because if recirculation is determined in the first assessment, then the procedure will have to be repeated several times in a trial and error procedure when adjusting the needles or the pump speed. Moreover, there is an increased risk of infection due to injections in access lines. Variability in the rate of manual injection of the saline bolus also introduces error to the recirculation measurement.

Recently, Tattersall et al., infra describe "a simpler method" for detecting and measuring recirculation. This method involves simultaneous sampling of blood (three sites) from the arterial and venous lines and from a peripheral vein. Each sample is submitted to a clinical laboratory for a urea determination. It is assumed that if there is recirculation within the blood access, the urea concentration in the arterial line is lower than in the peripheral vein because of mixing with dialyzed blood which has recirculated from the venous access device. The fraction of blood entering the arterial access device which has recirculated directly from the venous access device is termed the recirculation fraction (RF) and is calculated from the three measured urea fractions. This has become the most commonly used procedure to calculate recirculation. Also, the urea measurements require a clinical lab (and considerable expense) and the results may not be obtained until the next day, long after the dialysis procedure has been completed. However, there is increased variability due to clinical laboratory errors in measuring BUN (blood urea nitrogen).

Therefore, there is a need in the art for a rapid recirculation detection procedure and device that provides real time information and that enables convenient multiple measurements of recirculation following needle or equipment adjustment. There is a further need in the art for a recirculation measurement method that does not use expensive equipment, introduce an invasive procedure, laboratory analysis, or require a break in the dialysis method to take a recirculation measurement. The present invention was made to address each of the foregoing unmet needs.

SUMMARY OF THE INVENTION

The present invention provides a method for rapidly and inexpensively determining the amount of recirculation in a patient undergoing a hemodialysis treatment comprising measuring temperature of an arterial limb and a venous limb of a dialysis access, decreasing temperature of blood being returned to the patient from about 0.5° C. to about 30° C. or increasing temperature of blood being returned to the patient from about 0.5° C. to about 8° C. without adding volume, and measuring temperature of the arterial limb and the venous limb of the dialysis access to determine if there is a temperature drop or increase in the arterial limb as evidence of recirculation. The amount of recirculation will be proportional to the temperature change at the arterial limb. Preferably, the temperature is decreased or increased from about 1° C. to about 8° C. in blood being returned to the patient. Preferably, the method for decreasing temperature is to cool the dialysate being used for the dialysis procedure or to cool the venous tubing set. Preferably, temperature measurements are made by means of any device that can measure temperature of blood in a tube or in an access device, directly or indirectly, such as a thermometer, a liquid crystal display, infra-red display, thermistor, or infrared light.

The present invention further provides an improved blood tubing set for use in dialysis and for simultaneously determining recirculation according to the inventive method herein, comprising a blood tubing set having an arterial limb comprising an arterial access device and an arterial tube and having a venous limb comprising a venous access device and a venous tube, wherein an access device comprises a means for obtaining or returning blood from or to an individual, wherein the improvement comprises a means for measuring temperature in the arterial limb and a means for measuring temperature in the venous limb. Preferably, the means for measuring temperature comprises a temperature probe in the arterial tube and a temperature probe in the venous tube, or the temperature probes can be located in the arterial access device and the venous access device.

BRIEF DESCRIPTION OF THE DRAWING

FIG. 1 illustrates a diagram of a recirculation device used to calculate experimental recirculation in vitro simulating dialysis and recirculation. This device was used in the experiment reported in Example 1.

FIG. 2 shows a graph from five experiments where the dialysate temperature was dropped from 5° C. and 10° C. and its effects monitored at location Temp 2 (FIG. 1) showing recirculation rates from 0% to 30%. This Figure shows a reproducible direct relationship between percentage recirculation and amount of the temperature drop.

FIG. 3 shows an effect of recirculation and relationship with Temp 2 (FIG. 1). Temp 1 was kept constant at 26° C. and recirculation was varied from 0 to 40%.

FIG. 4 illustrates the relationship between arterial temperature increase (left panel) and decrease (right panel) as a function of recirculation.

DETAILED DESCRIPTION OF THE INVENTION

Definitions

Figure 5:
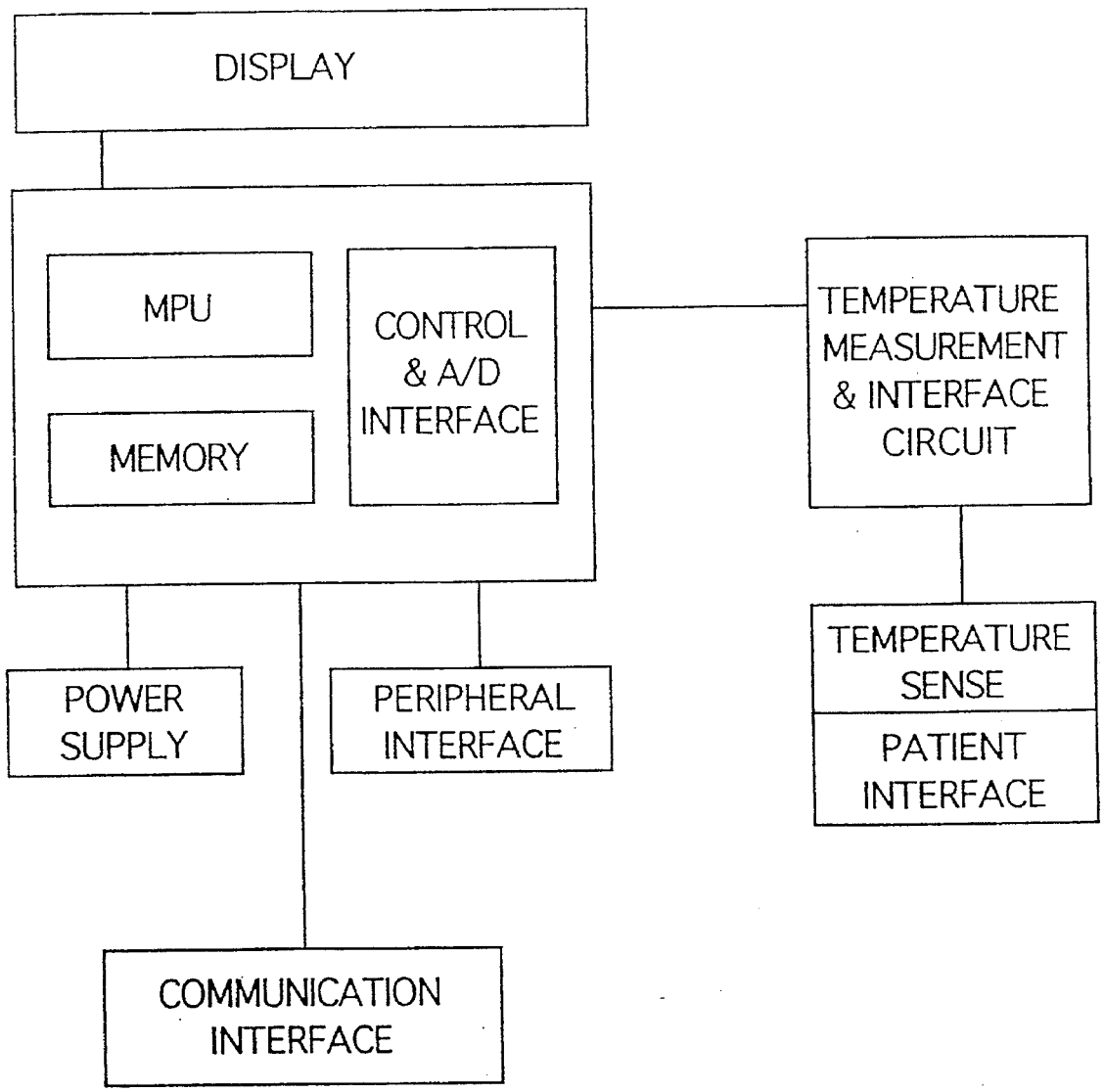
FIG. 5 illustrates a block diagram of a device that is used to calculate recirculation when two temperature measurements and blood pump flow rates are used as input. The device can automatically adjust pump speeds and determine if such will reduce recirculation.

The present invention utilizes terms that have the following meanings:

Access Device is any means through which blood can be withdrawn from or returned to the patient, such as a needle, catheter or cannula.

Arterial shall mean blood that is taken from the patient and directed to a dialyzer.

Blood Tubing Set are plastic tubes which conduct blood through a dialysis machine and from and to the patient.

Catheter is a plastic tube inserted into a blood vessel of the patient and used to get and return blood from and to the patient.

Hemodialysis is a method for purifying blood by passing it into a cartridge called a dialyzer.

Vascular Dialysis Access consists of a fistula, graft or catheters.

Venous shall mean blood being returned to the patient from the dialyzer.

The present invention provides a method for rapidly and inexpensively determining the amount of recirculation in a patient undergoing a dialysis treatment, comprising measuring temperature of an arterial limb and a venous limb of a blood access, decreasing or increasing temperature of blood being returned to the patient without adding volume, and measuring temperature of the arterial limb and the venous limb of the blood access to determine if there is a temperature change in the arterial limb as evidence of recirculation. The temperature is decreased or increased from about 0.5° C. to about 30° C., without adding volume, in blood being returned to the patient. However, if the temperature of blood is increased, it is not increased above 45° C. to avoid damaging the blood. Preferably, the temperature is decreased or increased from about 1° C. to about 10° C. in blood being returned to the patient. The method for decreasing temperature is to cool the dialysate being used for the dialysis procedure below its normal operating temperature of about 38° C. for a short period of time so as to enable the recirculation measurement to be made.

Alternatively, one can cool the venous tubing set by means of a refrigeration device or cooling means being attached to the tubing set. The method for increasing temperature is to heat the dialysate being used for the dialysis procedure above its normal operating temperature of about 38° C. (to, for example, 42° C.) for a short period of time so as to enable the recirculation measurement to be made. Alternatively, one can heat the venous tubing set by means of a heating device or heating means being attached to the tubing set.

Temperature measurements can be made by means of a temperature probe in or on each of the arterial tubing set and the venous tubing set. Alternatively, a temperature probe can be placed in the arterial access device and in the venous access device. The temperature probe can be either added to the outside of the tubing set for the recirculation measurement, or preferably, a tubing set is constructed having a temperature probe embedded in each of the arterial and venous lines. Similarly, a temperature probe can be constructed with an associated needle, catheter or any other access device. By "associated with" is implied that a temperature probe may be embedded within, on the outside of or within the lumen of an access device to order to measure the temperature of blood, directly or indirectly, within the access device. An access device, for example, comprises needles and catheters in combination or alone.

The present invention further comprises an electronic means to conduct recirculation calculations in real time to provide information to immediately reconfigure a dialysis treatment with a patient to provide a most efficient dialysis treatment possible. One example of such an electronic means is shown in FIG. 4. In a preferred embodiment, an electronics control comprises a microprocessor-based system comprising a microprocessor circuit, wherein the microprocessor circuit comprises a microprocessor, memory, control and analog-to-digital (A/D) interface circuits, a temperature measurement and interface circuit, a temperature sensor and patient interface circuit, a peripheral interface, and a communication interface. The interconnections are shown in FIG. 4. The microprocessor interprets and decodes program instructions stored in a Read Only Memory (ROM) section and sets up control circuits accordingly. The microprocessor receives input from the peripheral interface when a switch is activated or a preset condition is met. The microprocessor receives temperature information in digital form, after analog to digital conversion if necessary, and processes such information for storage or decision making as illustrated in a software flow chart (FIG. 5). The microprocessor can also send processed information to a display section for visual display or to data storage.

The interface circuit provides a means for creating compatibility between the temperature sensor circuit and the analog to digital interface circuit. The interface circuit comprises a signal amplification circuit, a level translation and reference signals needed for temperature measurement. The temperature sensor and patient comprises temperature sensors placed as provided herein, patient interface circuits, isolation and thermal conduction elements. The peripheral interface comprises switches for command inputs to the system (e.g., keyboard). The commands are interpreted to initiate or terminate a task. The communication interface connects the electronic system to any means for outside communication, such as other computers or a modem. In addition, the electronic system comprises a means for displaying information and a power supply.

Figure 6:
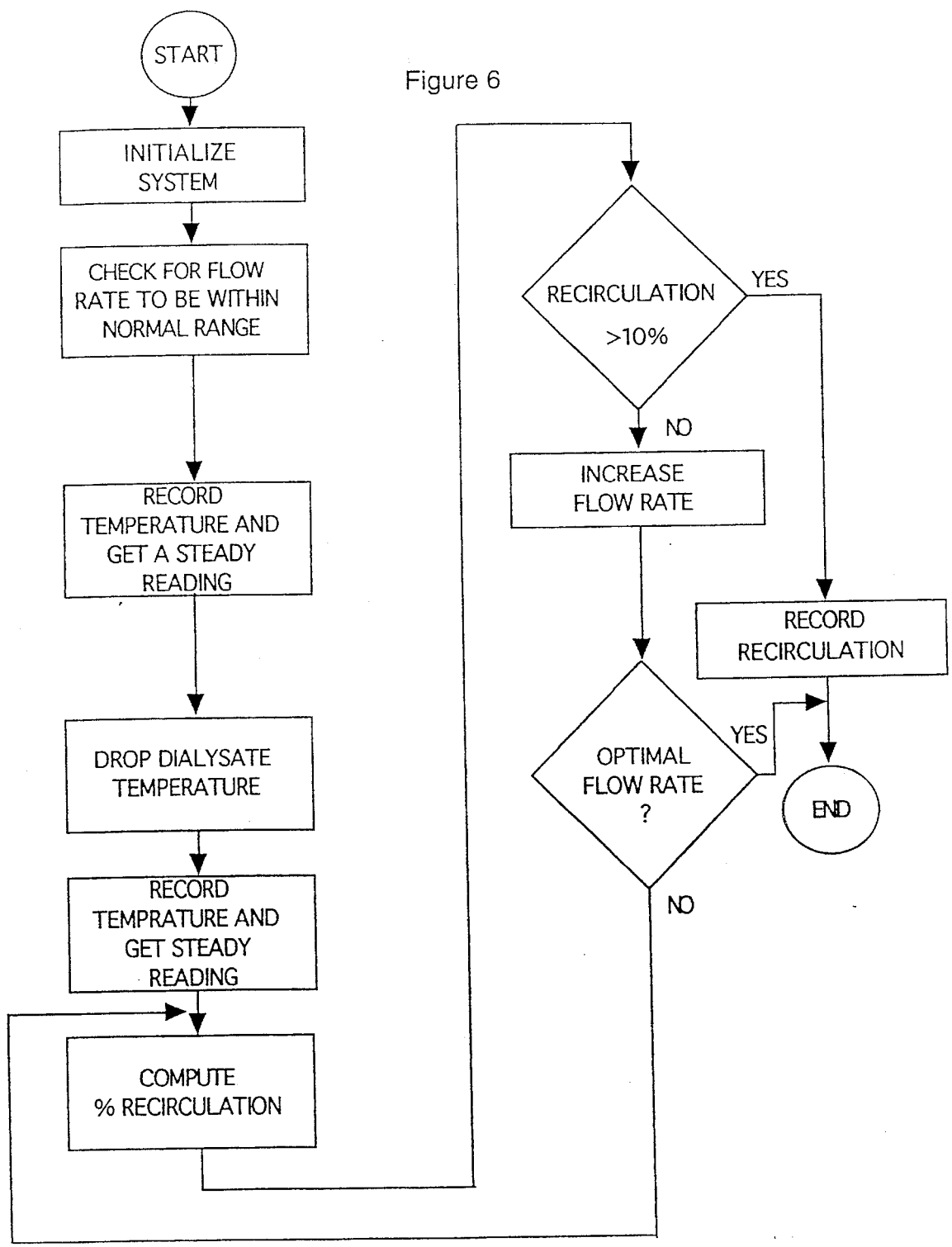
FIG. 6 illustrates a flow chart of the software system of the inventive device that can be used to automatically determine recirculation and make patient adjustments without the need for extensive operator assistance.

The electronic system is controlled by a software program. For example a flow chart of a preferred software program is shown in FIG. 6. The software operates with six major decision steps sequentially. These include a means for initializing the system, a means for setting the flow rate to a normal value, a means for recording the temperature measurements at each of at least temperature sensors, a means to control a change in temperature of blood being returned to the patient, a means for making a second temperature recording, and a means for computing the percentage of recirculation and a means for adjusting flow rate to recalculate the percentage recirculation as described above. With regard to the means for initializing the system, this is activated when power is first applied to the system or a reset command is issued. The means for initializing the system resets all the input and output ports to their initial state, checks the integrity of Random Access Memory (RAM) for read and write operation and initializes the system for known values in different memory locations. The means for initializing the system sets up counter, stack pointer and various registers for initial values. Any program interrupts are disabled until initialization is complete.

After the system is initialized, a prompt is issued to the operator (via a display means) to set the flow rate within a normal treatment range. This step is necessary to establish a basis to achieve optimal operating conditions. The software further monitors blood temperature at each of the sites and the temperature is recorded when a steady reading is obtained. A steady reading is a temperature reading that remains stable for at least three seconds. Each temperature reading that is recorded is stored and used for recirculation coefficient computation. The dialysate temperature is then changed as provided in the inventive method herein. The operator is prompted to adjust dialysate temperature. Temperature measurements are monitored and recorded when a steady reading is obtained. Such temperature readings are stored as T (recirculation).

The present invention further provides an improved blood tubing set for use in dialysis and for simultaneously determining recirculation according to the inventive method herein, comprising a blood tubing set having an arterial limb comprising an arterial access device and an arterial tube and having a venous limb comprising a venous access device and a venous tube wherein the improvement comprises a means for measuring temperature in the arterial limb and a means for measuring temperature in the venous limb. Preferably, the means for measuring temperature comprises a temperature probe in the arterial tube or arterial access device and a temperature probe in the venous tube or venous access device.

The inventive method and inventive tubing set provides a cost savings for dialysis procedures because the invention obviates the need for expensive clinical laboratory procedures to measure BUN (blood urea nitrogen) levels (three blood samples) in the arterial limb, venous limb and "periphery". Moreover, the present invention provides a real time measurement with instant information to the operator whether or not there is recirculation and the percentage of recirculation experienced by a patient. Lastly, the inventive recirculation measurement does not require expensive equipment or the necessity of severely slowing down dialysis in order to obtain an accurate recirculation measurement as the procedure described in Greenwood et al., infra. This allows corrective measures to be taken during treatment and not days later if one has to wait for clinical lab results. Moreover, when coupled to the inventive device, corrective measures can be taken automatically without even the need for operator intervention. The inventive device, blood tubing set and method results in eliminating a problem of blood handling to obtain urea measurements from a clinical laboratory and reduces the risk of contamination to the blood sample and from the blood sample if the patient is infected with, for example, HIV or hepatitis.

Additional benefits of the present invention include a fully automated device that can be used to automatically readjust pump speeds without extensive operator assistance, and eliminates much trial and error procedure to make adjustments that would eliminate patient recirculation. This allows for instant corrective measures and the net result is a faster and more efficient dialysis treatment with cost savings.

Once recirculation is determined and if it is too high, it can be reduced by adjusting the needles or by adjusting pump speed. If these procedures do not work upon a new recirculation measurement, there may be blockage problems with the fistula that may require surgical intervention for correction. Therefore, the present invention has utility to determine if surgical repair is needed in the fistula or if simple adjustments to the needles or pump speed can correct a recirculation problem and increase dialysis efficiency.

The following examples illustrate several features of the inventive blood tubing set, method and device. The examples are intended to illustrate several features of the invention, and are not to be construed as limiting the scope of the claimed invention.

EXAMPLE 1

This example illustrates a relationship between temperature measurement and recirculation to validate the utility of the present invention. An in vitro dialysis/recirculation device was constructed and is illustrated in FIG. 1. Specifically, a dialyzer was connected to a dialysate circuit and to a simulated patient and access with two loops of tubing with the dialysate circuit and simulated patient and access each having independent pumping and temperature control means. In FIG. 1, the top loops represents a dialysate circuit, and the middle loop represents a blood circuit of the in vitro simulated device. The bottom loop and container in FIG. 1 represents blood access and patient blood, respectively with independent Pump3 representing the blood pump.

Temperatures of the liquid used was measured at four locations depicted in FIG. 1 and labeled as Temps 1–4. Pump2 in the simulated patient and access loop was used to regulate the amount of recirculation. Temp3 (the "patient")

was kept constant at 40° C. throughout the experiments. Temp2 was observed at recirculation rates varying from 0 to 30% (as controlled by pump 2).

In five experiments, the dialysate temperature (Temp1) was lowered by varying mounts (ranging from 5° C. to 10° C.) and the effects at Temp2 were recorded at recirculation rates varying from 0% to 30%. These data are shown in Table 1 below. We found a direct relationship between the recirculation rate and the size of the temperature drop at Temp2. FIG. 2 shows the average values of temperature changes at the arterial limb (Temp2) as a result of changes in dialysate temperature (Temp 1) and recirculation rate (Pump2). Both Temp3 and Pump3 were not altered.

In a separate experiment, Temp 1 was kept constant at 26° C. and recirculation was varied from 0% to 40%. The effect of recirculation and its relationship to Temp2 is shown in FIG. 3. There was a direct relationship between the recirculation rate and temperature at Temp2. In another experiment, Temp 1 was held constant at 34.5° C. and recirculation was varied from 0 to 45%. As seen in FIG. 4, there was a direct relationship between changes in temperature at Temp2 and recirculation rate.

EXAMPLE 2

This example provides two additional experiments where a dialysis machine was used to conduct a simulated dialysis. Dialysate was used on both sides of the dialysis machine. The experimental setup was similar to the diagram described in FIG. 1, except the dialysate circuit was replaced by a hemodialysis machine. The temperature of the dialysate used was dropped to 34 ° C. and the recirculation was changed between 0 and 45%. A direct relationship between Temp2 and recirculation is shown in Tables 1 and 2 below.

TABLE 1

| % Recirculation | Dialysate | Venous | Arterial | min Arterial | max Arterial | Av. "Body" |
|---|---|---|---|---|---|---|
| 0 | 37.5 | 857 | 897 | | 897 | 37.2 |
| 0 | 34.5 | 670 | 870 | | 870 | 37.2 |
| 5 | 34.5 | 659 | 810 | | 810 | 37.3 |
| 10 | 34.5 | 661 | 830 | | 830 | 37.2 |
| 15 | 34.5 | 671 | 803 | 818 | 810.5 | 37.3 |
| 20 | 34.5 | 671 | 788 | 802 | 795 | 37.2 |
| 25 | 34.5 | 665 | 774 | 782 | 778 | 37.2 |
| 30 | 34.5 | 670 | 771 | 783 | 777 | 37 |
| 35 | 34.5 | 675 | 762 | 772 | 767 | 37.1 |
| 40 | 34.5 | 679 | 754 | 759 | 756.5 | 37.1 |
| 45 | 34.5 | 678 | 745 | 752 | 748.5 | 37.1 |
| 40 | 34.5 | 683 | 755 | 761 | 758 | 37.1 |
| 35 | 34.5 | 678 | 763 | 768 | 765.5 | 37.1 |
| 30 | 34.5 | 677 | 776 | 786 | 781 | 37.2 |
| 25 | 34.5 | 682 | 786 | 793 | 789.5 | 37.1 |
| 20 | 34.5 | 679 | 797 | 805 | 801 | 37.1 |
| 15 | 34.5 | 679 | 812 | 826 | 819 | 37.2 |
| 10 | 34.5 | 675 | 831 | 835 | 833 | 37.1 |
| 5 | 34.5 | 680 | 850 | 864 | 857 | 37.1 |
| 0 | 34.5 | 678 | 873 | 892 | 882.5 | 37.1 |

TABLE 3

| Body Temp | Recirc. % | Art. Temp. | Body Temp. | Recirc % | Art. Temp. |
|---|---|---|---|---|---|
| 40 | 0 | 38 | 36.869 | 0 | 35.693 |
| 40 | 5 | 38 | 36.642 | 5 | 35.484 |
| 40 | 10 | 38 | 36.547 | 10 | 34.729 |
| 40 | 15 | 38 | 35.962 | 15 | 34.819 |
| 40 | 20 | 38 | 35.761 | 20 | 34.693 |
| 40 | 25 | 38 | 35.681 | 25 | 34.476 |
| 40 | 30 | 38 | 35.356 | 30 | 34.386 |
| 40 | 35 | 38 | 35.018 | 35 | 34.212 |
| 40 | 40 | 38 | 34.935 | 40 | 34.111 |
| 40 | 45 | 38 | 34.700 | 45 | 33.848 |
| 40 | 40 | 38 | 34.855 | 40 | 33.910 |
| 40 | 35 | 38 | 34.967 | 35 | 34.079 |
| 40 | 30 | 38 | 35.159 | 30 | 34.186 |
| 40 | 25 | 38 | 35.446 | 25 | 34.501 |
| 40 | 20 | 38 | 35.821 | 20 | 34.649 |
| 40 | 15 | 38 | 36.170 | 15 | 34.873 |
| 40 | 10 | 38 | 36.289 | 10 | 35.125 |
| 40 | 5 | 38 | 36.730 | 5 | 35.473 |
| 40 | 0 | 38 | 37.120 | 0 | 35.727 |

Therefore, the data provided herein with the in vitro dialysis device allows a predictive model of the value of the inventive method and inventive blood tubing set to rapidly and reliable determine recirculation in a patient.

EXAMPLE 3

Figure 7:
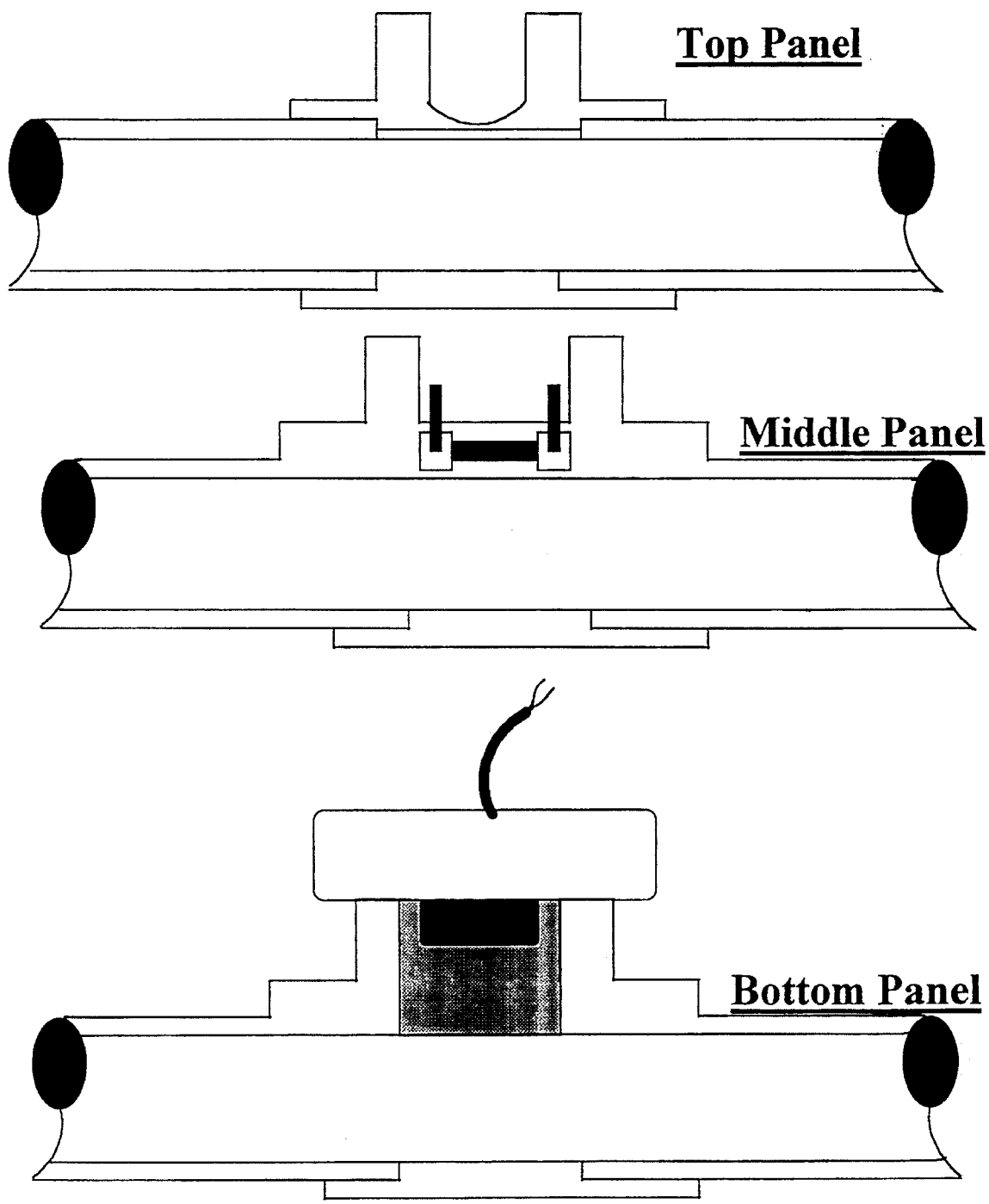
FIG. 7 shows several examples of tubing set configurations and where the temperature probe can measure temperature of blood by air conductance or solid conductance via the material of the tubing (top panel), by being molded within the tubing material (middle panel), or by being in contact with a temperature conducting medium, such as a gel material (bottom panel).

This example illustrates examples of configurations of an inventive tubing set having a temperature probe. There are three examples of how a temperature probe can be added to a tubing set (see FIG. 7) that satisfy the requirement that the temperature probe measure accurately the relative temperature of the blood circulating within the tubing set. Preferably, there is an insulation means (not shown in FIG. 7) that surrounds the temperature probe to prevent the external environment from influencing the temperature reading.

The examples of temperature probes include a temperature probe embedded within the plastic walls of the tubing set. Other examples include a cavity for insertion of a temperature probe and a heat-conducting gel-filled cavity that allows for thermal contact of the temperature probe with circulating blood.

What is claimed is:

1. A method for determining the amount of recirculation in a patient undergoing a dialysis treatment, comprising measuring temperature of an arterial limb and a venous limb of a dialysis access, changing temperature of blood being returned to the patient without adding volume, and measuring temperature of the arterial limb and the venous limb of the dialysis access to determine if there is a temperature change in the arterial limb to determine the amount of recirculation.

2. The method of claim 1 wherein the temperature of blood is changed by decreasing it from about 0.5° C. to about 30° C. in blood being returned to the patient.

3. The method of claim 2 wherein the temperature of blood is changed by decreasing it from about 1° C. to about 10° C. in blood being returned to the patient.

4. The method of claim 1 wherein the method for decreasing temperature of blood comprises either cooling the dialysate being used for the dialysis procedure or cooling the venous tubing set.

5. The method of claim 1 wherein the temperature of blood is changed by increasing it from about 0.5° C. to about 3° C. in blood being returned to the patient.

* * * * *